United States Patent
Friess et al.

(10) Patent No.: US 6,740,127 B2
(45) Date of Patent: May 25, 2004

(54) AGENT AND METHOD FOR COLORING KERATIN FIBRES

(75) Inventors: Gabriele Friess, Gross-Umstadt (DE); Iris Bahnmueller, Weinheim (DE)

(73) Assignee: Wella Aktiengellschaft, Darmstadt (DE)

(*) Notice: Subject to any disclaimer, the term of this patent is extended or adjusted under 35 U.S.C. 154(b) by 145 days.

(21) Appl. No.: 09/979,597

(22) PCT Filed: Mar. 7, 2001

(86) PCT No.: PCT/EP01/02556

§ 371 (c)(1), (2), (4) Date: Nov. 16, 2001

(87) PCT Pub. No.: WO01/70182

PCT Pub. Date: Sep. 27, 2001

(65) Prior Publication Data

US 2002/0189029 A1 Dec. 19, 2002

(30) Foreign Application Priority Data

Mar. 22, 2000 (DE) .......................... 100 14 149

(51) Int. Cl.⁷ ................................. A61K 7/13
(52) U.S. Cl. .............. 8/405; 8/406; 8/408; 8/410; 8/412; 8/415; 8/421; 8/423; 8/437; 8/570
(58) Field of Search ................. 8/405, 406, 408, 8/410, 412, 415, 421, 423, 437, 570

(56) References Cited

U.S. PATENT DOCUMENTS

| | | | | |
|---|---|---|---|---|
| 4,311,478 A | * | 1/1982 | Bugaut et al. | 8/407 |
| 5,478,359 A | | 12/1995 | LaGrange et al. | 8/412 |
| 5,718,731 A | * | 2/1998 | Loewe et al. | 8/409 |
| 5,961,667 A | | 10/1999 | Doehling et al. | 8/408 |

FOREIGN PATENT DOCUMENTS

| | | |
|---|---|---|
| DE | 1 810 191 | 10/1973 |
| DE | 299 09 427 U | 7/1999 |
| EP | 0 692 245 A | 1/1996 |
| EP | 0 891 971 A | 1/1999 |

* cited by examiner

Primary Examiner—Brian P. Mruk
Assistant Examiner—Elisa Elhilo
(74) Attorney, Agent, or Firm—Michael J. Striker

(57) ABSTRACT

The preparation for dyeing keratin fibers contains, in a cosmetic carrier, a combination of at least one 4,5-diaminopyrazole derivative of formula (I), or a physiologically compatible salt thereof.

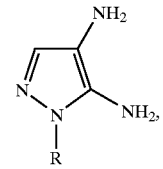

(I)

in which R is an alkyl group, a monohydroxyalkyl group, a polyhydroxyalkyl group, a monoaminoalkyl group, a polyaminoalkyl group, an unsubstituted benzyl group or a substituted benzyl group substituted with a halogen, an alkyl group or an alkoxy group; and at least one phenylurea derivative of formula (II), or a physiologically compatible salt thereof,

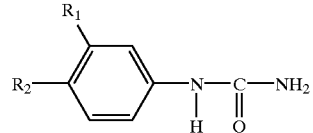

(II)

in which R1 represents a hydroxyl or alkoxy group and R2 represents a hydrogen atom, a halogen atom, an alkyl group, an alkoxy group, a hydroxyalkyl group or polyhydroxyalkyl group, each with up to 6 carbon atoms. A method of hair dyeing with this preparation is described.

11 Claims, No Drawings

AGENT AND METHOD FOR COLORING KERATIN FIBRES

BACKGROUND OF THE INVENTION

The present invention relates to a preparation for dyeing keratin fibers, especially of human hair, which contains at least one 4,5-diaminopyrazole derivative and at least one phenylurea derivative. Dyeings of keratin fibers are carried out in that the above-mentioned composition is mixed with an oxidizing agent, applied on the fibers and, after a specified period of action, washed out once again.

The use of phenylureas in dyeing agents is known from the literature. For example, in the German patent 18 10 191, dyeing agents are described, which contain a combination of phenylureas with 1,4-diaminobenzene or 2,5-diaminotoluene sulfate. However, with these agents, the fibers can only be dyed blue, green or violet with a strong blue tint. The German utility model 299 094 27 discloses dyeing agents, which contain, among other things, a combination of certain pyrazoles and N-(3-dimethylamino)-phenylurea. However, these preparations also do not produce a red tint.

There was therefore a continued need for dyeing agents based on phenylurea derivatives, which make brilliant, intensive, pure red tints possible.

SUMMARY OF THE INVENTION

Surprisingly, it has now been found that, when a combination of 4,5-diaminopyrazoles of formula (I) and phenylureas of formula (II) are used, an intensive, brilliant, red oxidative dyeing of the hair is possible, intensive pure red tints being obtained even without the addition of further oxidation dye precursors.

The object of the present application therefore is a preparation for dyeing keratin fibers, which is mixed with an oxidizing agent before use and is characterized in that it contains, in a suitable cosmetic carrier, a combination of at least one 4,5-diaminopyrazole derivative of the general formula (I) or its physically compatible salts

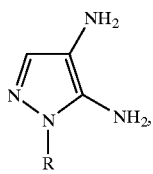
(I)

in which R is a linear or branched alkyl group with 1 to 6 carbon atoms, a linear or branched monohydroxyalkyl group with 1 to 6 carbon atoms, a linear or branched polyhydroxyalkyl group with 2 to 6 carbon atoms, a linear or branched monoaminoalkyl group with 1 to 6 carbon atoms, a linear or branched polyaminoalkyl group with 2 to 6 carbon atoms, a benzyl group, substituted with a halogen atom, a linear or branched alkyl group with 1 to 6 carbon atoms or a linear or branched alkoxy group with 1 to 6 carbon atoms or an unsubstituted benzyl group, and at least one phenylurea derivative of the general formula (II) or its physiologically compatible salts,

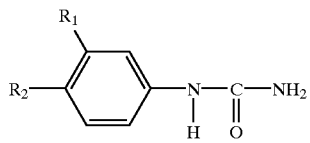
(II)

in which R1 represents a hydroxyl group, an amino group, a linear or branched alkylamino group with 1 to 6 carbon atoms, a linear or branched dialkylamino group with 2 to 6 carbon atoms, a linear or branched alkoxy group with 1 to 6 carbon atoms and R2 represents a hydrogen atom, a halogen atom, a linear or branched alkyl group with 1 to 6 carbon atoms, a linear or branched alkoxy group with 1 to 6 carbon atoms, a linear or branched hydroxyalkyl group with 1 to 6 carbon atoms or a linear or branched polyhydroxyalkyl group with 2 to 6 carbon atoms with the proviso that R2 is not hydrogen when R1 is a dialkylamino group.

Especially preferred derivatives of the general formula (I) are the following compounds or their physiologically compatible salts:
4,5-diamino-1-methyl-1H-pyrazole; 4,5-diamino-1-(4'-methylbenzyl)-pyrazole; 4,5-diamino-1-(2'-hydroxyethyl)-1H-pyrazole; 4,5-diamino-1-benzyl-1H-pyrazole; 4,5-diamino-1-ethyl-1H-pyrazole; 4,5-diamino-1-isopropyl-1H-pyrazole; 4,5-diamino-1-(4'-methoxybenzyl)-1H-pyrazole; 4,5-diamino-1H-pyrazole; 4,5-diamino-1-(3'-methoxybenzyl)-1H-pyrazole and 4,5-diamino-1-(4'-chlorobenzyl)-1H-pyrazole.

Especially preferred derivatives of the general formula (II) are the following compounds or their physiologically compatible salts:
3-ureido-phenol, 2-chloro-5-ureido-phenol, 2-methyl-5-ureido-phenol, 2-methoxy-5-ureido-phenol, 3-amino-4-methyl-phenylurea and 3-amino-4-methoxy-phenylurea.

Although the inventive dye combination leads to excellent red dyeings already without the addition of further dyes, further oxidation dye precursors, such as derivatives of p-phenylenediamine, like 2-(2',5'-diaminophenyl)ethanol, resorcinol derivates such as resorcinol, 2-methylresorcinol or 4-chlororesorcinol, amino and hydroxy derivatives of 1,3-benzodioxol, naphthalene derivates, such as 1-hydroxynaphthalene, 1,5-dihydroxynaphthalene or 1,7-dihydroxynaphthalene, as well as direct dyes such as 2-amino-4,6-dinitrophenol, 2-ethylamino-4,6-dinitrophenol, 2-[(2'-hydroxyethyl)amino]-4,6-dinitrophenol, 2-amino-6-chloro-4-nitrophenol or 2-chloro-6-ethylamino-4-nitrophenol can be added to the inventive dyeing agent in order to round off the dyeing results.

The compounds of formulas (I) and (II), like the above-described oxidative and direct dyes can be used in the form of the free base as well as in the form of their physiologically compatible salts with organic or inorganic acids, such as hydrochloric acid, phosphoric acid, sulfuric acid, acetic acid, lactic acid or citric acid, especially in the form of the hydrochlorides or sulfates. In the case of phenols, these compounds can also be present as alkali phenolates.

The total concentration of dye precursor in the inventive dyeing preparation is about 0.1 to 20% by weight and preferably 0.2 to 6% by weight. The concentration of the compounds of formulas (I) and (II) as well as of the oxidation dye precursors and direct dyes is about 0.01 to 5% by weight and preferably 0.1 to 4% by weight.

Moreover, the usual cosmetic additives, such as antioxidants like ascorbic acid, thiogylcolic acid or sodium sulfite, perfume oils, complexing agents, wetting agents, emulsifiers, thickeners, grooming materials and other auxiliary materials and additives, suitable for cosmetic agents, may be contained in the inventive dyeing preparation as a component of the cosmetic carrier.

Before, as well as after it is mixed with the oxidizing agent, the inventive dyeing preparation may be prepared, for example, in the form of a solution, especially an aqueous or aqueous-alcoholic solution, a cream or a gel or an emulsion. Its composition represents a mixture of the dyeing components with additives, which are customary for such preparations.

Conventional additives in solutions, creams, emulsions or gels are, for example, solvents, such as water, low molecular weight aliphatic alcohols such as ethanol, n-propanol and isopropanol or glycols, such as glycerin and 1,2-propylene glycol, furthermore wetting agents or emulsifiers from the classes of anionic, cationic, amphoteric or non-ionic surface active substances, such as fatty alcohol sulfates, ethoxylated fatty alcohol sulfates, alkyl sulfonates, alkylbenzenesulfonates, alkyltrimethylammonium salts, alkylbetaines, ethoxylated fatty alcohols, ethoxylated nonylphenols, fatty acids alkanolamides, ethoxylated fatty alcohols, ethoxylated nonylphenols, fatty acid alkanolamides, ethoxylated fatty esters, furthermore thickeners such as higher molecular weight fatty alcohols, starch or cellulose derivatives, furthermore Vaseline, paraffin oil and fatty acids, as well as grooming materials, such as cationic resins, lanolin derivatives, cholesterol, pantothenic acid and betaine. The aforementioned components are used in amounts, customary for such purposes. For example, the wetting agents and emulsifiers are used in concentrations of about 0.5 to 30% by weight (based on the dye carrier composition), the thickeners are used in an amount of about 0.1 to 25% by weight (based on the dye carrier composition) and the grooming agents are used in a concentration of about 0.1 to 5.0% by weight (based on the dye carrier composition).

Directly before use, the inventive hair-dyeing agent is mixed with a liquid oxidizing agent in a suitable ratio. The dyeing agent and the oxidizing agent are mixed together preferably in a ratio by weight of about 5:1 to 1:3, a ratio by weight of 1:1 to 2:2 being particularly preferred.

The pH of the ready-for-use inventive hair dyeing agent, resulting from mixing the preferably alkaline dye carrier composition with the generally acidic oxidizing agent, is affected by the amount of alkali in the dye carrier composition and the amount of acid in the oxidizing agent as well as by the mixing ratio. The pH of the finished hair-dyeing agent is between about 3 and 11 and preferably between 5 and 9.

For adjusting the pH of the dye carrier composition and the oxidizing agent, organic and inorganic acids, such as phosphoric acid, ascorbic acid and lactic acid, or alkalis, such as monoethanolamine, triethanolamine, 2-amino-2-methyl-1-propanol, ammonia, sodium hydroxide solution, potassium hydroxide solution or tris-(hydroxymethyl)-aminomethane can be used depending on the pH that is desired.

When used for the oxidative dyeing of hair, the inventive dyeing agent, described above, is mixed immediately before use with the oxidizing agent and is applied on the hair in an amount, which is sufficient for the hair dyeing treatment and, depending on the fullness of the hair, is in general between about 60 and 200 g of the ready-for-use oxidizing dyeing agent obtained.

As oxidizing agent, mainly hydrogen peroxide or its addition compounds with urea, melamine or sodium bromate in the form of a 1 to 12% and preferably 6% aqueous solution, comes into consideration, hydrogen peroxide being particularly preferred.

The inventive dyeing agent is allowed to act for about 10 to 45 minutes and preferably 25 to 40 minutes (and particularly 30 minutes) on the hair at 15° C. to 50° C., after which the hair is rinsed with water and dried. Optionally, after this rinsing, the hair is washed with a shampoo and possibly rinsed with a weak organic acid, such as citric acid or tartaric acid. Subsequently, the hair is dried.

The following examples are intended to explain the object of the invention in greater detail without limiting it to these examples.

EXAMPLES

Example 1

Oxidation Hair Dye, Alkaline

| | |
|---|---|
| 10.00 g | isopropanol |
| 10.00 g | lauryl alcohol diglycol ether sulfate sodium salts, (28% aqueous solution) |
| 10.00 g | ammonia (25% aqueous solution) |
| 0.30 g | ascorbic acid |
| 1.50 g | 4,5-diamino-1-(4'-methylbenzyl)-1H-pyrazole sulfate |
| 0.92 g | 3-ureido-phenol |
| ad 100.00 g | water, fully deionized |

The pH of the hair-dyeing solution is 10.5.

Before use, 10 g of the hair dyeing solution, described above, is mixed with 10 g of a hydrogen peroxide solution (6% solution in water). The ready-for-use oxidation dyeing agent, which is so obtained and has a pH of 9.5 to 9.8, is applied on the hair. After a period of action of 30 minutes at 40° C., the hair is rinsed with water, shampooed and dried. The hair receives an intensive raspberry red coloration.

Example 2

Oxidation Hair Dye, Alkaline

| | |
|---|---|
| 2.00 g | 4,5-diamino-1-(2'-hydroxyethyl)-1H-pyrazole sulfate |
| 1.56 g | 2-chloro-5-ureido-phenol |
| 15.00 g | cetylalcohol |
| 3.50 g | lauryl alcohol diglycol ether sulfate sodium salts, (28% aqueous solution) |
| 3.00 g | ammonia (25% aqueous solution) |
| 0.30 g | sodium sulfite, anhydrous |
| ad 100.00 g | water, fully deionized |

The pH of the hair dyeing cream is 10.5.

Immediately before use, 10 g of the hair dyeing cream, described above, is mixed with 10 g of a hydrogen peroxide solution (6% solution in water). The ready-for-use oxidation dyeing agent, which is so obtained and has a pH of 9.5 to 9.8, is applied on the hair. After a period of action of 30 minutes at 40° C., the hair is rinsed with water and dried. The hair, so treated, has a brilliant pink coloration.

Example 3

Oxidation Hair Dye, Alkaline

| | |
|---|---|
| 2.05 g | 4,5-diamino-1-benzyl-1H-pyrazole sulfate |
| 1.53 g | 2-methyl-5-ureido-phenol |
| 0.40 g | sodium hydroxide, solid |
| 0.60 g | ascorbic acid |
| 7.00 g | isopropanol |
| 15.00 g | oleic acid |
| 10.00 g | ammonia (25% aqueous solution) |
| ad 100.00 g | water, fully deionized |

The pH of the hair dyeing gel is 10.5.

Immediately before use, 10 g of the hair dyeing gel, described above, is mixed with 10 g of a hydrogen peroxide solution (6% solution in water). The ready-for-use oxidation dyeing agent, which is so obtained and has a pH of 9.5 to 9.8, is applied on the hair. After a period of action of 40 minutes at 35° C., the hair is rinsed with water and dried. A brilliant red-orange coloration of the hair is obtained.

Example 4

Oxidation Hair Dye, Alkaline

| | |
|---|---|
| 10.00 g | isopropanol |
| 10.00 g | lauryl alcohol diglycol ether sulfate sodium salts, (28% aqueous solution) |
| 10.00 g | ammonia (25% aqueous solution) |
| 0.30 g | ascorbic acid |
| 3.00 g | 4,5-diamino-1-isopropyl-1H-pyrazole sulfate |
| 1.92 g | 3-ureido-phenol |
| ad 100.00 g | water, fully deionized |

The pH of the hair dyeing solution is 10.5.

Immediately before use, 10 g of the hair dyeing solution, described above, is mixed with 10 g of a hydrogen peroxide solution (6% solution in water). The ready-for-use oxidation dyeing agent, which is so obtained and has a pH of 9.5 to 9.8, is applied on the hair. After a period of action of 30 minutes at 40° C., the hair is rinsed with water and dried. The hair is dyed an intensive raspberry red.

Example 5

Oxidation Hair Dyeing Agent—Acidic

| | |
|---|---|
| 10.00 g | isopropanol |
| 10.00 g | lauryl alcohol diglycol ether sulfate sodium salts, (28% aqueous solution) |
| 10.00 g | ammonia (25% aqueous solution) |
| 0.30 g | ascorbic acid |
| 1.50 g | 4,5-diamino-1-(4'-methylbenzyl)-1H-pyrazole sulfate |
| 0.92 g | 3-ureido-phenol |
| ad 100.00 g | water, fully deionized |

The pH of the hair dyeing solution is 10.5.

Before use, 10 g of the hair dyeing solution, described above, is mixed with 10 g of a hydrogen peroxide solution (6% solution in water) and the ready-for-use oxidation dyeing agent, so obtained, is adjusted to a pH of 6.8 with phosphoric acid. Subsequently, the oxidation dyeing agent is applied on the hair. After a period of action of 30 minutes at 40° C., the hair is rinsed with water, shampooed and dried. The hair is dyed an intensive raspberry red.

Example 6

Oxidation Hair Dyeing Agent—Acidic

| | |
|---|---|
| 2.00 g | 4,5-diamino-1-(2'-hydroxyethyl)-1H-pyrazole sulfate |
| 1.56 g | 2-chloro-5-ureido-phenol |
| 15.00 g | cetyl alcohol |
| 3.50 g | lauryl alcohol diglycol ether sulfate sodium salts, (28% aqueous solution) |
| 3.00 g | ammonia (25% aqueous solution) |
| 0.30 g | sodium sulfite, anhydrous |
| ad 100.00 g | water, fully deionized |

The pH of the hair dyeing cream is 10.5.

Immediately before use, 10 g of the hair dyeing cream, described above, is mixed with 10 g of a hydrogen peroxide solution (6% solution in water) and the ready-for-use oxidation dyeing agent, so obtained, is adjusted to a pH of 6.8 with phosphoric acid. Subsequently, the oxidation dyeing agent is applied on the hair. After a period of action of 30 minutes at 40° C., the hair is rinsed with water and dried. The hair, so treated, has a brilliant pink coloration.

What is claimed is:

1. A preparation for dyeing keratin fibers, said preparation comprising, in a cosmetic carrier, a combination of at least one 4,5-diaminopyrazole derivative of formula (I), or a physically compatible salt thereof,

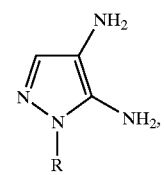

(I)

in which R is a linear or branched alkyl group with 1 to 6 carbon atoms, a linear or branched monohydroxyalkyl group with 1 to 6 carbon atoms, a linear or branched polyhydroxyalkyl group with 2 to 6 carbon atoms, a linear or branched monoaminoalkyl group with 1 to 6 carbon atoms, a linear or branched polyaminoalkyl group with 2 to 6 carbon atoms, a benzyl group substituted with a halogen atom, a benzyl group substituted with a linear or branched alkyl group having 1 to 6 carbon atoms, a benzyl group substituted with a linear or branched alkoxy group having 1 to 6 carbon atoms or an unsubstituted benzyl group; and at least one phenylurea derivative of formula (II), or a physiologically compatible salt thereof,

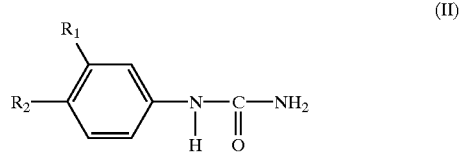

(II)

in which R1 represents a hydroxyl group or a linear or branched alkoxy group with 1 to 6 carbon atoms and R2 represents a hydrogen atom, a halogen atom, a linear or branched alkyl group with 1 to 6 carbon atoms, a linear or branched alkoxy group with 1 to 6 carbon atoms, a linear or branched hydroxyalkyl group with 1 to 6 carbon atoms or a linear or branched polyhydroxyalkyl group with 2 to 6 carbon atoms, wherein said combination leads to the formation of a red coloration.

2. The preparation as defined in claim 1, wherein said at least one 4,5-diaminopyrazole derivative of formula (I) is selected from the group consisting of 4,5-diamino-1-methyl-1H-pyrazole; 4,5-diamino-1-(4'-methylbenzyl)-pyrazole; 4,5-diamino-1-(2'-hydroxyethyl)-1H-pyrazole; 4,5-diamino-1-benzyl-1H-pyrazole; 4,5-diamino-1-ethyl-1H-pyrazole; 4,5-diamino-1-isopropyl-1H-pyrazole; 4,5-diamino-1-(4'-methoxybenzyl)-1H-pyrazole; 4,5-diamino-1H-pyrazole; 4,5-diamino-1-(3'-methoxybenzyl)-1H-pyrazole and 4,5-diamino-1-(4'-chlorobenzyl)-1H-pyrazole.

3. The preparation as defined in claim 1 or 2, wherein the at least one phenylurea derivative of formula (II) is selected from the group consisting of 3-ureido-phenol, 2-chloro-5-ureido-phenol, 2-methyl-5-ureido-phenol and 2-methoxy-5-ureido-phenol.

4. The preparation as defined in claim 1 or 2, further comprising at least one oxidation dye precursor selected from the group consisting of p-phenylenediamine derivatives, resorcinol derivatives, amino derivatives of 1,3-benzodioxol, hydroxy derivatives of 1,3-benzodioxol and naphthalene derivatives.

5. The preparation as defined in claim 1 or 2, further comprising direct dyes.

6. The preparation as defined in claim 1 or 2, containing from 0.01 to 5% by weight of said at least one 4,5-diaminopyrazole derivative of formula (I) and from 0.01 to 5% by weight of said at least one phenylurea derivative of formula (II).

7. The preparation as defined in claim 1 or 2, having a total dye concentration of 0.1 to 20% by weight.

8. A ready-to-apply hair dyeing agent made by mixing a hair dye preparation with an oxidizing agent in a weight ratio of said hair dye preparation to said oxidizing agent of about 5:1 to 1:3,
wherein the hair dye preparation comprises, in a cosmetic carrier, a combination of
at least one 4,5-diaminiopyrazole derivative of formula (I), or a physically compatible salt thereof,

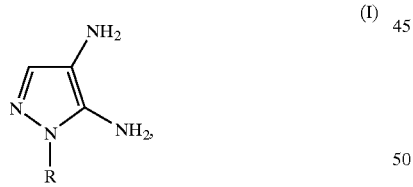
(I)

in which R is a linear or branched alkyl group with 1 to 6 carbon atoms, a linear or branched monohydroxyalkyl group with 1 to 6 carbon atoms, a linear of branched polyhydroxyalkyl group with 2 to 6 carbon atoms, a linear or branched monoaminoalkyl group with 1 to 6 carbon atoms, a linear or branched polyaminoalkyl group with 2 to 6 carbon atoms, a benzyl group substituted with a halogen atom, a benzyl group substituted with a linear or branched alkyl group having 1 to 6 carbon atoms, a benzyl group substituted with a linear or branched alkoxy group having 1 to 6 carbon atoms or an unsubstituted benzyl group; and at least one phenylurea derivative of formula (II), or a physiological compatible salt thereof,

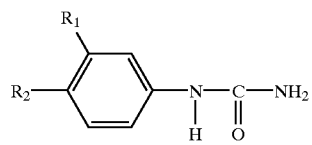
(II)

in which R1 represents a hydroxyl group or a linear or branched alkoxy group with 1 to 6 carbon atoms and R2 represents a hydrogen atom, a halogen atom, a linear or branched alkyl group with 1 to 6 carbon atoms, a linear or branched alkoxy group with 1 to 6 carbon atoms, a linear or branched hydroxyalkyl group with 1 to 6 carbon atoms or a linear or branched polyhydroxyalkyl group with 2 to 6 carbon atoms, wherein said combination leads to the formation of a red coloration.

9. The ready-to-apply hair dyeing agent as defined in claim 8, having a pH of from 3 to 11.

10. A method of dyeing hair, said method comprising the steps of:

a) mixing a hair dye preparation with an oxidizing agent to form a ready-to-apply hair dyeing agent immediately prior to application of the hair dyeing agent;

b) applying the ready-to-apply hair dyeing agent to the hair in an amount sufficient for the dyeing of the hair;

c) allowing the ready-to-apply hair dyeing agent applied to the hair during the applying to act on the hair for an acting time interval of 10 to 45 minutes at a temperature of 15° C. to 50° C.;

d) after said acting time interval, rinsing the hair with water, optionally shampooing the hair and then drying the hair;

wherein the hair dye preparation comprises, in a cosmetic carrier, a combination of
at least one 4,5-diaminopyrazole derivative of formula (I), or a physically compatible salt thereof,

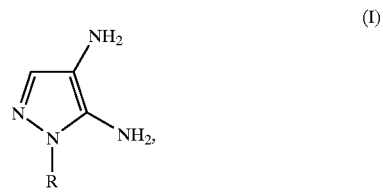
(I)

in which R is a linear or branched alkyl group with 1 to 6 carbon atoms, a linear or branched monohydroxyalkyl group with 1 to 6 carbon atoms, a linear or branched polyhydroxyalkyl group with 2 to 6 carbon atoms, a linear or branched monoaminoalkyl group with 1 to 6 carbon atoms, a linear or branched polyaminoalkyl group with 2 to 6 carbon atoms, a benzyl group substituted with a halogen atom, a benzyl group substituted with a linear or branched alkyl group having 1 to 6 carbon atoms, a benzyl group substituted with a linear or branched alkoxy group having 1 to 6 carbon atoms or an unsubstituted benzyl group; and at least one phenylurea derivative of formula (II), or a physiologically compatible salt thereof,

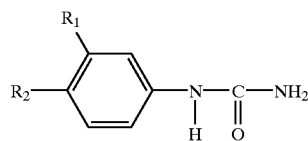

in which R1 represents a hydroxyl group or a linear or branched alkoxy group with 1 to 6 carbon atoms and R2 represents a hydrogen atom, a halogen atom, a linear or branched alkyl group with 1 to 6 carbon atoms, a linear or branched alkoxy group with 1 to 6 carbon atoms, a linear or branched hydroxyalkyl group with 1 to 6 carbon atoms or a linear or branched polyhydroxyalkyl group with 2 to 6 carbon atoms, wherein said combination leads to the formation of a red coloration.

11. The method as defined in claim 10, wherein said hair dye preparation is mixed with said oxidizing agent in a weight ratio of said dye preparation to said oxidizing agent of about 5:1 to 1:3.

* * * * *